US012396495B1

(12) United States Patent
Agam et al.

(10) Patent No.: US 12,396,495 B1
(45) Date of Patent: Aug. 26, 2025

(54) PANTS THAT CAN ACCOMMODATE A CATHETER

(71) Applicants: Nitza Agam, Daly City, CA (US); Lalit K. Goel, Sunnyvale, CA (US)

(72) Inventors: Nitza Agam, Daly City, CA (US); Lalit K. Goel, Sunnyvale, CA (US)

(*) Notice: Subject to any disclaimer, the term of this patent is extended or adjusted under 35 U.S.C. 154(b) by 648 days.

(21) Appl. No.: 18/143,199

(22) Filed: May 4, 2023

(51) Int. Cl.
*A61F 5/44* (2006.01)
*A41D 1/06* (2006.01)
*A44B 19/00* (2006.01)
*A44B 19/26* (2006.01)

(52) U.S. Cl.
CPC ............. *A41D 1/06* (2013.01); *A44B 19/265* (2013.01); *A61F 5/4408* (2013.01)

(58) Field of Classification Search
CPC ........ A41D 1/06; A44B 19/265; A61F 5/4408
See application file for complete search history.

(56) References Cited

U.S. PATENT DOCUMENTS

| | | | | | |
|---|---|---|---|---|---|
| 2,484,356 | A | * | 10/1949 | Ribeiro | A61F 5/4401 604/347 |
| 3,353,538 | A | * | 11/1967 | Carrigan | A61F 5/453 604/352 |
| 4,022,213 | A | * | 5/1977 | Stein | A61F 5/453 604/350 |
| 4,319,571 | A | * | 3/1982 | Winchell | A61F 5/445 604/342 |
| 4,553,968 | A | * | 11/1985 | Komis | A41B 9/023 604/351 |
| 4,568,340 | A | * | 2/1986 | Giacalone | A61F 5/453 2/405 |
| 4,588,397 | A | * | 5/1986 | Giacalone | A61F 5/453 604/351 |
| 4,673,401 | A | * | 6/1987 | Jensen | A61F 5/44 604/353 |
| 4,713,066 | A | * | 12/1987 | Komis | A61F 5/453 604/351 |
| 4,813,943 | A | * | 3/1989 | Smith | A61F 5/4408 604/350 |
| 4,820,291 | A | * | 4/1989 | Terauchi | A61F 5/451 4/144.3 |
| 4,838,883 | A | * | 6/1989 | Matsuura | A61F 5/4408 604/353 |
| D311,805 | S | * | 11/1990 | Hayko | A61F 5/453 D2/745 |

(Continued)

OTHER PUBLICATIONS

Internet—https://www.silverts.com/discover-silvert Silverts sells Men's Easy Zipper Pants areare great for catheters.

(Continued)

*Primary Examiner* — Guy K Townsend
(74) *Attorney, Agent, or Firm* — Reston Law Group

(57) ABSTRACT

Pants housing a catheter that drains to a collection bag, said pants having a left and a right panel, wherein each panel is a covering element has a continuous zipper tape that is coextensive with the fabric forming a pant, wherein the panels provide a selectable portlets to the collection bag mounted on a wearer's anterior thigh to activate drainage or to service a connection of the catheter to the collection bag, and a selectable port to inspect, tighten straps and/or replace the collection bag. It is anticipated that the wearer may be in a wheelchair when these actions are performed.

11 Claims, 3 Drawing Sheets

(56) References Cited

U.S. PATENT DOCUMENTS

| | | | | |
|---|---|---|---|---|
| 5,053,027 | A * | 10/1991 | Manfredi | A61F 5/455 604/327 |
| 5,263,947 | A * | 11/1993 | Kay | A61L 24/043 604/351 |
| 5,409,475 | A * | 4/1995 | Steer | A61F 5/453 604/352 |
| 5,496,300 | A * | 3/1996 | Hirsch | A61F 5/4404 604/905 |
| 5,632,736 | A * | 5/1997 | Block | A61F 5/455 206/581 |
| 5,645,541 | A * | 7/1997 | Bouser | A61F 5/453 604/351 |
| 5,797,890 | A * | 8/1998 | Goulter | A61F 5/4405 604/351 |
| 5,827,247 | A * | 10/1998 | Kay | C08L 5/04 604/327 |
| 5,957,904 | A * | 9/1999 | Holland | A61F 5/455 604/352 |
| 6,477,710 | B1 * | 11/2002 | Ojoyeyi | A41D 13/1236 2/254 |
| 7,186,245 | B1 * | 3/2007 | Cheng | A61F 5/44 604/350 |
| 7,418,741 | B2 * | 9/2008 | Rogers | A41D 13/1236 2/114 |
| 7,594,279 | B2 * | 9/2009 | Roy | A41D 13/1236 2/114 |
| 7,673,348 | B2 * | 3/2010 | Williams | A41D 13/1236 2/244 |
| 8,607,366 | B2 * | 12/2013 | Austin | A41D 13/1272 604/174 |
| 8,690,835 | B1 * | 4/2014 | Parris | A41D 13/1236 604/179 |
| 8,832,864 | B1 * | 9/2014 | Braden | A41D 13/1272 2/114 |
| 10,159,594 | B2 * | 12/2018 | DeShazer | A61F 5/451 |
| 10,264,831 | B1 * | 4/2019 | Hemker | A61F 5/03 |
| 10,524,526 | B2 * | 1/2020 | Voy | A47G 29/08 |
| 10,750,801 | B2 * | 8/2020 | Bentley | A41D 13/1245 |
| 10,799,386 | B1 * | 10/2020 | Harrison, Sr. | A61F 5/441 |
| 11,202,477 | B1 * | 12/2021 | Dawson | A41D 31/02 |
| 11,382,371 | B2 * | 7/2022 | Bentley | A41D 27/201 |
| 11,510,445 | B2 * | 11/2022 | Bentley | A41D 13/1281 |
| 11,529,252 | B2 * | 12/2022 | Glithero | A61F 5/453 |
| 2002/0193763 | A1 * | 12/2002 | Kulikov | A61F 5/453 604/350 |
| 2004/0176746 | A1 * | 9/2004 | Forral | A61F 5/453 604/544 |
| 2004/0226073 | A1 * | 11/2004 | McCullar | A41D 13/1245 2/114 |
| 2006/0015082 | A1 * | 1/2006 | Pearson | A61F 5/453 604/347 |
| 2009/0112171 | A1 * | 4/2009 | Ng | A61F 5/44 604/327 |
| 2012/0165768 | A1 * | 6/2012 | Sekiyama | A61F 5/453 604/353 |
| 2013/0237964 | A1 * | 9/2013 | Kicos | A61F 5/4408 604/347 |
| 2013/0338617 | A1 * | 12/2013 | Newton, Jr. | A61F 5/453 604/353 |
| 2015/0320583 | A1 * | 11/2015 | Harvie | A61F 5/441 604/351 |
| 2017/0128255 | A1 * | 5/2017 | DeShazer | A61F 5/451 |
| 2017/0311662 | A1 * | 11/2017 | Piña et al. | A41D 13/1254 |
| 2018/0098877 | A1 * | 4/2018 | Pierson | A61F 5/4405 |
| 2019/0364992 | A1 * | 12/2019 | Thomas | A41D 13/1245 |
| 2020/0390591 | A1 * | 12/2020 | Glithero | A61F 5/455 |
| 2021/0038423 | A1 * | 2/2021 | Mavrinac | A61F 5/443 |
| 2022/0054298 | A1 * | 2/2022 | Walthall | A61F 5/4404 |
| 2022/0054327 | A1 * | 2/2022 | Coluzzi | A61F 13/4915 |
| 2022/0062028 | A1 * | 3/2022 | Mitchell | A61F 5/4405 |
| 2022/0347004 | A1 * | 11/2022 | Newton | A61F 5/453 |
| 2023/0115636 | A1 * | 4/2023 | Coughlin | A61F 5/4408 604/327 |

OTHER PUBLICATIONS

Internet—https://www.buckandbuck.com/adaptive-clothing-guide/clothing-for-those-with-urinary-cathe ters.html sells a drainage bag cover, made by Adaptable Designs.

* cited by examiner

PANTS THAT CAN ACCOMMODATE A CATHETER

FIELD OF THE INVENTION

The present invention in general is pants for an individual who has been fitted with a catheter that drains urine from their bladder into at least one collection bag that is mounted on a frontal region of one or both of their legs. The catheter is typically a Foley catheter. The invented pants facilitate operation and care of the at least one collection bag.

BACKGROUND OF THE INVENTION

Silverts sells Men's Easy Zipper Pants online at https://www.silverts.com/discover-silverts, stating that the pants are great for arthritis, catheters & paralysis. The pants have a waist with a drawstring, 1 back pocket & 2 side pockets, and functional fly zippers to just below the knee with a VELCRO closure from the knee down. The pant leg is open at the bottom for hemming the pant leg. Silvert advertises that his pants are versatile, great for knee surgery, hip replacement, broken legs & catheters. The pants have two-way zippers that open fully for easy access to casts and catheters and are easy for anyone in a reclining position. Silvert's Easy Touch Closures helps daily tasks such as dressing and undressing, and assisted dressing or independent dressing. Side zippers are secured at the waist with easy touch tabs and end above the ankle to allow for hemming. Also available are Open back pants for people who need help in getting dressed or have limited mobility. These open-back pants are traditional in fabrication, but with two overlapping panels on the backside that are closed using snaps in the waistband. With multiple snaps along the waistband they can be easily adjusted. There is no teaching for accessing a urine collection bag.

Buck-and-Buck urinary catheter clothing at (https://www.buckandbuck.com/adaptive-clothing-guide/clothing-for-those-with-urinary-catheters.html) sells a drainage bag cover, made by Adaptable Designs. The cover, which is for a standard urinary drainage bag, provides some privacy for the person utilizing the drainage bag. While the cover conceals the urine drainage from view, it reportedly can be easily accessed for monitoring and emptying. Buck-and-Buck assert that the need for a urinary catheter does not have to cause difficulty with wearing certain styles of clothing. Any of the pants for men and women can have a Velcro opening sewn into the inseam or side seam, whichever is preferred to make the user more comfortable and to allow access for care and emptying of the urine collection bag. Buck-and-Buck assert that best infection control practice is to not disconnect the catheter port from the urine collection bag since the catheter port is a potential path for entry of bacteria into the body. Buck-and-Buck teach a comfortable 12 inch hook and loop closure on the inseam of the slacks, which allows the urine collection bag to be passed through the leg opening, wherein emptying urine would exit through the inseam of the clothing, or if the drainage bag is mounted on the slack's leg on an outside surface of the slacks. Alternatively, the drainage bag can be attached to the wheelchair. The integrity of the closed catheter and urinary drainage tubing can be maintained. A cover provides some privacy for the person wearing the urinary catheter.

SUMMARY OF THE INVENTION

The invention is pants for an individual who has been fitted with a catheter, wherein the catheter drains urine from their bladder into at least one collection bag mounted on a frontal region of one or more of their legs. The catheter is typically a Foley catheter. The invented pants facilitate operation and care of the at least one collection bag.

An aspect of the invention is that it provides easy access to a lower portion of a collection bag, wherein a valve on an outlet of the collection bag enables controlled drainage of the collection bag.

A second aspect of the invention is that a length of flexible plastic tubing can be fitted onto a tubular extension of a collection bag's outlet, therein enabling discharge of urine to a commode, a urinal, a bedpan, or any suitable vessel. A length of the flexible plastic tubing can be appropriately selected to extend the outlet to below the wearer's knee.

A third aspect of the invention is that it provides easy access to an upper portion of a collection bag, wherein an inlet to the collection bag is visibly connected to the catheter can be confirmed, and if there is or isn't any leakage. If there is leakage, the connection can be corrected, and a surrounding area can be cleaned. The easy access enables a determination of whether a new collection bag is needed, and the user can be attended if that is the case.

A fourth aspect of the invention is that it provides easy access to the collection bag. If straps need to be adjusted, adjustments can be made, depending on how the collection bag is fastened, and potentially a new collection bag can be installed.

A fifth aspect of the invention is that the access is selectable to be partial via a portlet or to be complete through a port, wherein the port provides access to the entire collection bag, and furthermore the invention can include access to a single collection bag on either leg and access to a left collection bag on a left leg and a right collection bag on a right leg.

A sixth aspect of the invention is that the pants are large enough to accommodate the wearer's the catheter, and made of a fabric that is sufficiently supple that the wearer can feel the catheter through the fabric, and shift the catheter as needed; and A final aspect of the invention is that a selected zipper tape closure conforms to curved applications, therein providing panels that under load will not yield (open), and wherein the selected zipper tape closure is more resistant than Velcro to becoming fouled with hair or detritus.

BRIEF DESCRIPTION OF THE DRAWINGS

The foregoing invention will become readily apparent by referring to the following detailed description and the appended drawing in which.

DETAILED DESCRIPTION OF THE INVENTION

Figure 1:
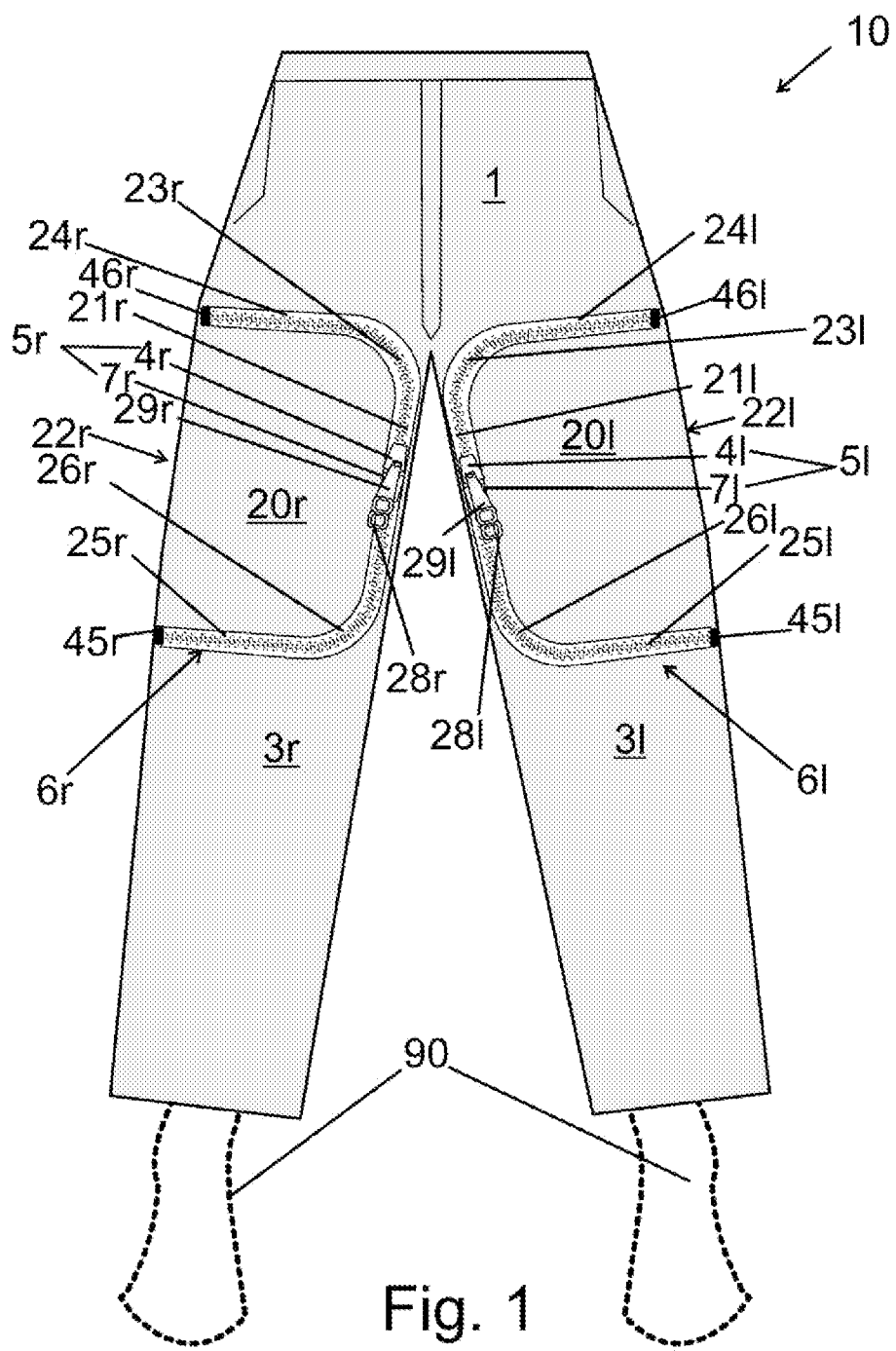
FIG. 1 is a frontal view of the invented pants, wherein at least one pant leg has a panel that provides access to a collection bag mounted frontally on a wearer's anterior thigh.

Invention 10 is pants 1, as shown in FIG. 1, for an individual who has been fitted with a catheter that drains urine from their bladder into at least one collection bag. The at least one collection bag is nominally mounted on a frontal region of one or both legs. The catheter is typically a Foley catheter. The invented pants facilitate the use and care of the at least one collection bag.

Figures 2, 3:
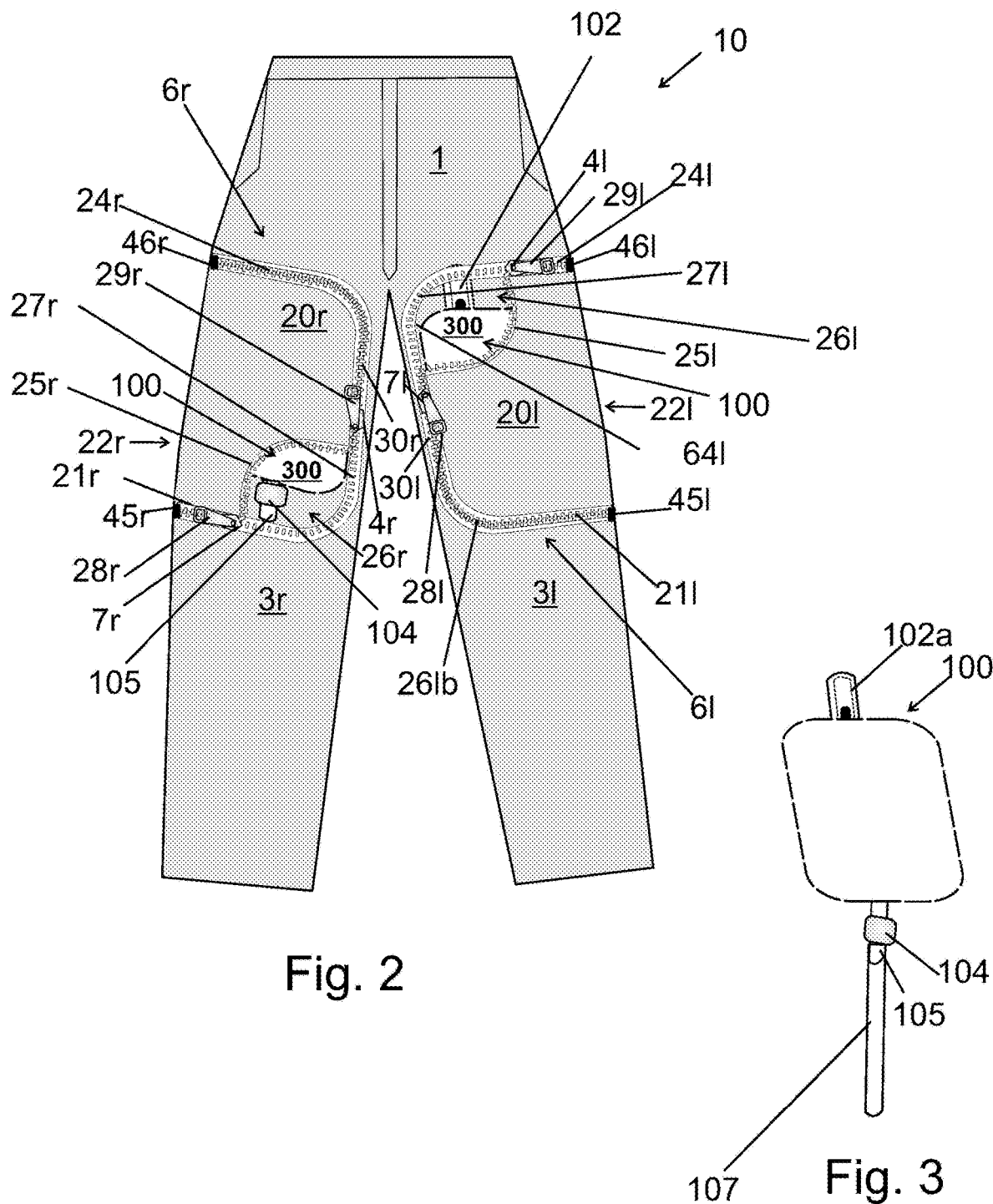
FIG. 2 is a frontal view of the invented pants that have a left panel and a right panel, wherein the illustrated panels are not limited, such that either or both panels can be closed as shown in FIG. 1, or partially open therein providing a portlet, or fully opened providing a port; and for illustrative purposes one panel has an upper portlet, and the other panel has a lower portlet of the other panel that is open.
FIG. 3 is a frontal view of a length of flexible plastic tubing fitted onto a tubular extension of the collection bag's drainage port outlet having the tubular extension, wherein the length of flexible plastic tubing is several inches long.
Figure 4:
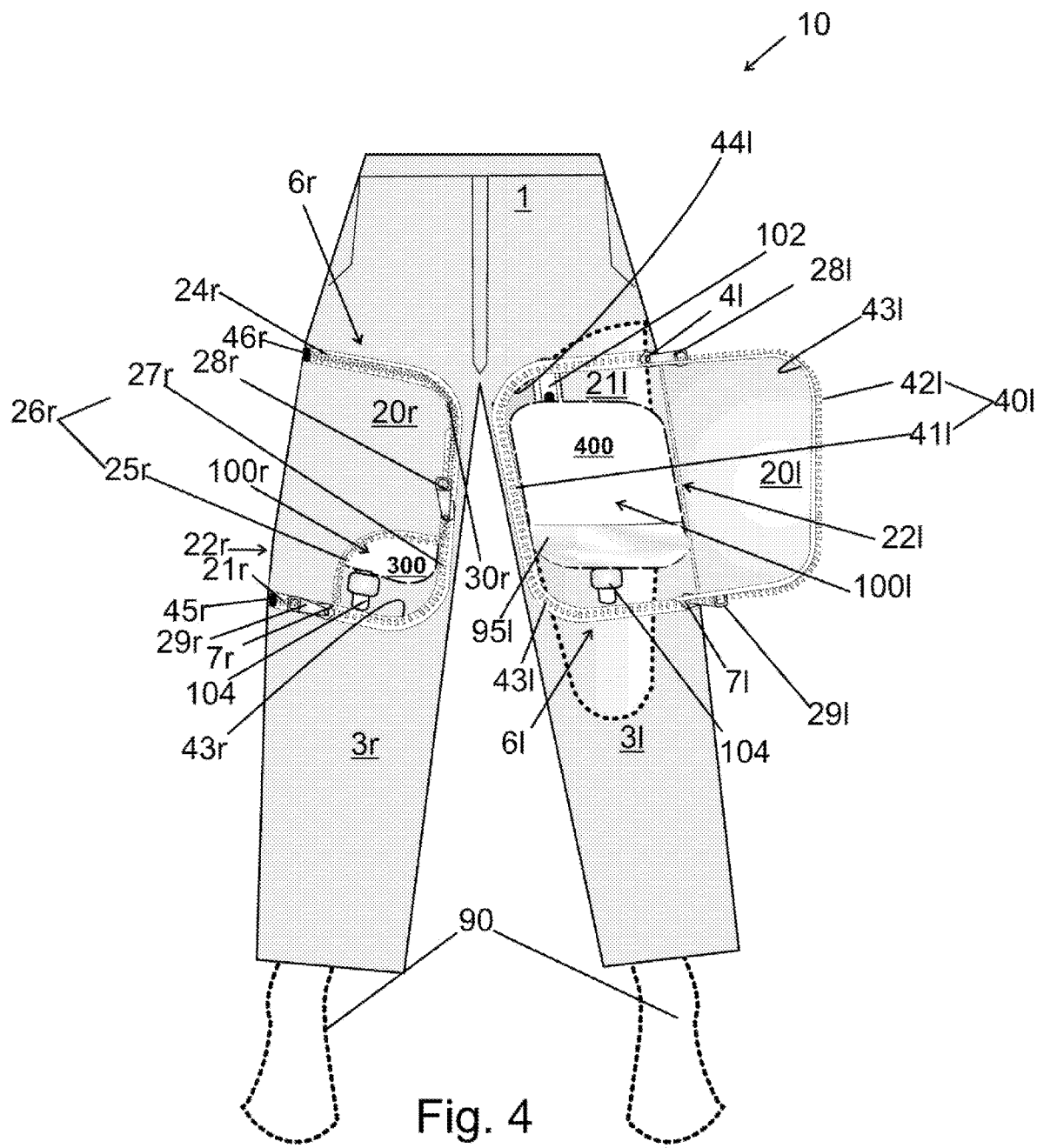
FIG. 4 is a frontal view of the invented pants, wherein currently the left panel is fully open creating a left port that provides a full view of the collection bag, the drainage outlet, and the inlet nor the collection bag are not elements of the instant invention, and therefore are shown with dashed lines; and as illustrated the right panel is partially open creating a right lower portlet.

At least one pant leg (3r,3l) has a panel 20r,20l that provides access to the collection bag 100. The collection bag 100 has an inlet 102 (as shown in FIGS. 2, 3 and 4), which connects to the catheter (not shown) that conveys urine to the collection bag. The collection bag also has an outlet 105 with a valve 104 (see FIGS. 2,4). The valve controls when urine is to be drained out of the collection bag 100. An exemplary collection bag 100 is shown in FIGS. 2 and 3). The invented pants can accommodate a wide selection of collection bags, and is not a limiting element of the invention. Similarly, The wearer's legs 90 are also shown with dashed lines.

The illustrated pants 1 have a left panel 20l and a right panel 20r, therein potentially enabling use and access to two collection bags. Each panel 20r,20l is secured by a shared continuous zipper tape 6r,6l and a lateral seam 22r,22l on each pant of the pants 1 covering the legs 3r,3i. The pants' fabric is nominally at least similar to each panel's fabric. The continuous zipper tape is shared by the panel's fabric and the pants' fabric, such that when fully zipped a left panel is coextensive with a left pant, and a right panel is coextensive with a right pant.

The shared continuous zipper tape 6r,6l includes a medial section 21r,21l that upwardly transition into an upper curved section 23r,23l; which laterally transitions into an upper horizontal section 24r,24l and ends in an upper stop 46r,46l. As illustrated, the medial section 21r,21l also downwardly transitions into a lower curved sections 26r,26l; which laterally transitions into to a lower horizontal section 25r,25l and ends in a lower stop 45r,45l. The shared continuous zipper tape spans an outer partial edge of a panel with an adjoining inner partial edge of an opening of the pant, therein connecting the partial edge of the panel to the inner partial edge of the opening of the pant.

In this configuration, each leg pant has a continuous zipper tape, which taken with the lateral seams 22r,22l defines the panels 20r,20l. Each of the shared continuous zipper tapes has a pair of zipper slide assemblies 5r,5l; where each zipper slide assembly includes a pair of opposing zipper slides 7r,4r and 7l,4l with locking pulls 28r,29r and 28l,29l for opening and closing all or partial portions of the zipper tapes 6r,6l. Note, each pair of opposing zipper slides 7r,4r and 7l,4l are aligned such that a pair of zipper slides are opposing and nose to nose. In this alignment when a left pair of slides are pulled apart, the left zipper tape 6l unzips and opens providing a portlet 300. The slides are pulled apart where a portlet is desired, as the pair separates the continuous zipper tape unzips, therein providing a portlet. The portlet cannot change in size or position because the locking pulls are locked except when they are being pulled. This is unlike hook and loop fasteners, which are not locked, and can continue to open or close, depending on factors such as load and tension.

When the pairs of opposing zipper slides 7r,4r and 7l,4l slides 7l,4l are pulled back together nose to nose, the zipper tape 6r,6l is rezipped and the portlet is closed.

The zipper assemblies 5r,5l are independent, and movement of the right slides 7r,4r does not affect movement of the left slides 7l,4l. This independence is in large part because the pulls 28r,29r and 28l,29l are locking pulls.

The zipper size is selected to be appropriate for the size of the pants. Smaller pants would typically have a size #4 or #4.5, which has a closed width of ~4 mm. Size #5 has a closed width of ~5 mm, and is typically strong enough for most adults. A size #10±#3 zipper could be used if the invented pants are for a very large individual.

In the instant invention, the environment nominally isn't very harsh, so molded tooth zippers are typically made of plastic, such as DuPont's Delrin® are not required, but could be preferred in special cases. Acetals are also suitable resins to mold into a zipper tape. An exemplary manufacturer is YKK®, and their line of molded tooth zippers is called Vision®. Lenzip® is another manufacturer of molded tooth zippers. Molded tooth zippers are strong and practically weatherproof and are urine proof. In general, molded tooth zippers are corrosion resistant.

Coil zippers utilize nylon teeth (Nylon® is also a DuPont plastic), wherein the teeth are sewn onto the side tape with polyester thread. Coil zipper teeth are stronger and more flexible than molded tooth zippers, making them better suited for curved applications. Polyester thread will break down in the sun, so coil zippers should be kept covered to protect them from extended UV exposure. Typical coil zippers are sizes #4.5, #5 and #10. Coil zipper tapes are advantageously nearly flat on the rear side.

Metal zippers have polished metal teeth that secure together on the zipper chain. Because they can corrode, they are typically only used indoors. Exemplary applications include bags and purses, backpacks, interior cushions and upholstery, and more. A potential downside of metal zippers is that metal zippers can have sharper edges, which potentially could scratch a collection bag, which is typically constructed of vinyl. Metal zippers are harder to stick than plastic zippers, as they will break a needle.

While coil zippers are preferred, they are not limiting as metal and molded tooth zippers can also be used in the disclosed invention. It is further anticipated that the opposing zipper tapes 6r,6l can include an overlying material tape and an underlying material tape onto the zipper tapes 6r,6l. Typically, basting tape is used to fasten zipper tapes to cloth materials, and fabric tapes. Basting tape is a narrow double-sided pressure sensitive adhesive tape on a release liner, often employed to facilitate mechanized stitching.

An example of the collection bag is sold by AMSure®, and it is called a urinary leg bag. The urinary leg bag can be secured to the leg with two adjustable elastic leg straps. The catheter leg bag easily connects to any Foley catheter. It has leak proof seams, which ensures fluid containment. It has two flexible, high-quality straps, to ensure secure attachment to either of the wearer's leg. The leg straps are soft and breathable. The urinary leg bag is an anti-reflux leg bag catheter bag, which helps improve patient safety by reducing urine backflow. It has either a push-pull or a twist-turn drainage port (aka outlet 105 with a valve 104). A medium size has a potential volume of 600 milliliters (~20 oz). The large size has a potential volume of 900 ml (~30 oz). The push-pull (valve 104) drainage port (also called the T-Tap drainage port) includes a tubular extension 105 with a sloped opening, as shown in FIG. 3.

It is anticipated that the instant invention 1 can include a length of flexible plastic tubing 107 fitted onto the collection bag's outlet 105, wherein a lower end of the outlet has the tubular extension. The length of flexible plastic tubing is several inches long, as illustrated in FIG. 3, therein extending the outlet below a wearer's knee, thereby facilitating periodic drainage directly into a commode or a bedpan.

FIG. 2 illustrates how an upper portion of the left panel 20*l* is opened creating the portlet 300. The zipper slide 4*l* is pulled, from an initial left central position of the left medial section 21*l* shown in FIG. 1, upward and through the upper left curve 27*l*, and then laterally to the upper horizontal section 24*l*, stopping at a point 24*l*, which is proximate to the stop 46*l* and proximate to a left seam 22*l* of the invented pants 1. The unzipped portion of the left panel 20*l* therein exposes an upper portion of the collection bag 100 and the inlet 102. The unzipped portion of panel 20*l* in FIG. 2 is bounded by a left set of inner teeth 25 and a left set of outer teeth 27*l* on the zipper tape 6*l*.

The unzipped portion of the zipper tape 6*l* provides the portlet 300 in an upper portion 261 of the left panel 20*l*, wherein the portlet illustrates how it provides access to the inlet 102 and to an upper portion of the collect bag. Note, that in this illustrated embodiment the outer teeth 27*l* are recessed on an underlying peripheral layer of fabric or other mater al that is affixed to the zipper material tape 64*l*. The underlying peripheral outer layer of fabric or other material provides a protective cover of the outer zipper teeth 27*l* on the pant from coming into contact with the collection bag. Optionally, the inner teeth 25*l* can also be recessed on a comparable underlying peripheral inner layer of fabric or other material to provide an inner protective cover of the inner zipper teeth 25*l* on the panel from coming into contact with the collection bag.

A preferred zipper type is a coil zipper, as the coil zipper is relatively fine-toothed, and it provides a smooth zip. Coil zippers are stronger and more flexible than molded tooth zippers, making them suitably operative for the curved surface of the invention. The zipper size is selected based on the size of the invented pants. For most applications size #5 is suitable. For very large individuals the size is #10±#3.

Optionally, a protective material tape as discussed above can be employed to keep the zipper covered, wherein the material tape protects the collection bag from contact with the zipper. Testing supports that Lenzip® sliders work with Lenzip® zipper chain and YKK® sliders work with a YKK® zipper chain.

FIG. 2 also illustrates a first operating element of the opposing zipper slides, which is that as the opposing zipper slides are partially pulled apart, the continuous zipper tape unzips therein providing a partial opening, which is a portlet 300 for the panels 20*l*,20*r*. The portlet 300 provides partial access to the collection bag, wherein said partial perimeter outer edge of the panel separates from said inner edge of the pant leg; wherein the portlet can be closed by pulling the opposing zipper slides together.

Another illustration of the portlet 300 is in a lower portion of the right panel 20*r*. The zipper slide 7*r* has been pulled from an initial right central position of the right medial section 21*r* shown in FIG. 1, downward and through the lower right curve 26*r*, and then laterally to the lower horizontal section 25*r*, stopping at a lower point 21*r*, which is proximate to a right seam 22*r* of the invented pants 1. The unzipped portion of the right panel 20*r* therein exposes, via the portlet 300, a lower portion 26*r* of the right panel 20*r*, which is normally covering the outlet 104, and the valve 105 on the lower portion of the collection bag 100. The unzipped portion of panel 20*r* in FIG. 2 is bounded by a right set of inner teeth 25*r* and a right set of outer teeth 27*r*.

The invented pants 1 in FIG. 4 illustrate a second operating element utilizing the left pair of opposing zipper slide assemblies 5*l*. As shown the opposing zipper slides assemblies 7*l*,4*l* having locking pulls 28*l*,29*l* are on the left continuous zipper tape 6*l* of the left panel 20*l*. As shown the slides have been pulled apart until the upper slide 4*l* abuts the upper left stop 46*l* and the lower slide 7*l* abuts the lower left stop 45*l* (see FIG. 1 as the slides and stops are obscured). The movement unzips the left continuous zipper tape 6*l*, such that the panel 20*l* can fold laterally therein providing a port 400 to the collection bag 100*l* and a portion of the left thigh of the left leg 90 is visible, and shown in dashed lines.

The left panel 20*l* is fully opened along the seam 22*l*, exposing an interior portion 21*l* of pant 3*l*. The pulls are locking, so there no movement of the slides 4*l*,7*l*. The fully unzipped continuous zipper tape is labelled 40*l*, with outer panel teeth 42*l*, and inner pant teeth 41*l*. The outer panel teeth 42*l* are mounted on the panel's portion of the zipper's side tape material 431, and the inner pant teeth 41*l* are mounted on the pant's portion of the zipper's side tape material 44*l*.

A view of how much urine 95*l* has been collected is easily discernable. The port 400 also provides a partial view of the straps, if present; and an inspection of the connection of the inlet to a catheter. The collection bag 100 shown in the left panel has a volume 95*l* of urine. The collection bag 100 shown in the right panel has no urine. Unless the right collection bag 100*r* is new, no urine can be indicative that there is a problem, for example: a leak at the inlet that connects to the catheter. A Foley catheter tends to a have small flow most of the time.

While not shown, likewise the right panel 20*r* can similarly be fully opened along the seam 22*r*, exposing an interior side of pant 3*r*, when the right opposing zipper slides 4*r*,7*r* are pulled to the stops 45*r*,46*r*, as shown in FIG. 1.

The port 400 can be closed by folding the panel inward and pulling the opposing zipper slides together, preferably to the medial position as shown in FIG. 1.

The pulls on the zipper assemblies are locking pulls, therein preventing premature closure of portlets 300 or ports 400.

Both the left and right panel provides a selectable portlet to the collection bag mounted on a wearer's frontal anterior thigh to activate drainage or to service a connection of the catheter to the collection bag, and a selectable port to inspect, tighten straps and/or replace the collection bag. It is anticipated that the wearer may be in a wheelchair when these actions are performed.

Although the present disclosure has been illustrated and described herein with reference to exemplary embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

Finally, any numerical parameters set forth in this Specification and the attached Claims are approximations (for example, by using the term "about") that may vary depending upon the desired properties sought to be obtained by the present invention. At the very least, and not as an attempt to limit the application of the doctrine of equivalents to the scope of the Claims, each numerical parameter should be construed in light of the number of significant digits and by applying ordinary rounding.

It is to be understood that the foregoing description and specific embodiments are merely illustrative of the best mode of the invention and the principles thereof, and that various modifications and additions may be made to the invention by those skilled in the art, without departing from the spirit and scope of this invention, which is therefore understood to be limited only by the scope of the appended claims.

What is claimed is:

1. Pants that can accommodate a catheter, wherein the catheter drains urine from a wearer's bladder to at least one collection bag, said pants comprising:
    a panel that is a covering component of a pant leg that can provide access to the at least one collection bag on a frontal anterior thigh of the wearer, wherein said panel provides partial and full access to the at least one collection bag as needed;
    wherein said panel has a lateral edge that is coextensive with a lateral seam of a pant, a partial perimeter outer edge that is closed by a shared continuous zipper tape with a pair of stops, where the partial perimeter outer edge of said panel is substantially coextensive with an inner edge of the pant leg;
    said shared continuous zipper tape has a zipper slide assembly with a pair of opposing zipper slides with locking pulls for opening and closing said shared continuous zipper tape, and by extension said panel;
    a first operating element of the opposing zipper slides is that as the opposing zipper slides are pulled apart, the continuous zipper tape unzips, therein providing a portlet at a position along the said shared continuous zipper tape;
    wherein the portlet can be closed by pulling the opposing zipper slides together; and
    a second operating element of the opposing zipper slides is that when the opposing zipper slides are pulled apart until individual slides of the pair of slides abut a upper stop and a lower stop, then the continuous zipper tape is unzipped therein providing a port, and the panel can be folded laterally along the lateral seam of the pant leg; and
    wherein the port can be closed by pulling the opposing zipper slides together.

2. Pants according to claim 1, wherein said pants further comprising:
    an abdominal region, which is large enough to accommodate the catheter.

3. Pants according to claim 1, wherein said pants further comprised of a fabric that is sufficiently supple that the wearer can feel the catheter through the fabric, to determine if the catheter needs adjustment.

4. Pants according to claim 1, wherein the shared continuous zipper tape comprises:
    a medial section that upwardly transitions into an upper curved section, which laterally transitions into an upper horizontal section ending in the upper stop; and the medial section also downwardly transitions into a lower curved section, which laterally transitions into to a lower horizontal section ending in the lower stop.

5. Pants according to claim 1, further comprises: a left panel on a left pant that is substantially a mirror image of a right panel on a right pant.

6. Pants according to claim 1, wherein the shared continuous zipper tape comprises: a coil zipper tape.

7. Pants according to claim 1, wherein the pulls on the zipper assemblies comprises: locking pulls, which prevent accidental closure of the portlet or the port.

8. Pants according to claim 1, further comprising: a length of flexible plastic tubing that is several inches long, therein extending the outlet of the collection bag below a wearer's knee, thereby facilitating periodic drainage into a commode, urinal or a bedpan, or any suitable vessel.

9. Pants according to claim 6, further comprising:
    said shared continuous zipper tape is selected from the group consisting of: a size #4, #4.5 or #5 for most pants.

10. Pants according to claim 6, further comprising:
    said shared continuous zipper tape is selected from size #10±#3 for very large pants.

11. Pants according to claim 1, wherein the continuous zipper tape comprises: a combination of outer teeth mounted on a panel's side tape and inner teeth mounted on a pant's side tape.

* * * * *